(12) United States Patent
Wilkins (10) Patent No.: US 10,499,805 B2
(45) Date of Patent: Dec. 10, 2019

(54) VISUAL STRESS ASSESSMENT DEVICE (71) Applicant: University of Essex Enterprise Limited, Colchester, Essex (GB)

(72) Inventor: Arnold Wilkins, Cambridge (GB)

(73) Assignee: University of Essex Enterprise Limited, Colchester, Essex (GB)

(*) Notice: Subject to any disclaimer, the term of this patent is extended or adjusted under 35 U.S.C. 154(b) by 22 days.

(21) Appl. No.: 15/766,970

(22) PCT Filed: Oct. 21, 2016

(86) PCT No.: PCT/GB2016/053301
§ 371 (c)(1),
(2) Date: Apr. 9, 2018

(87) PCT Pub. No.: WO2017/072496
PCT Pub. Date: May 4, 2017

(65) Prior Publication Data
US 2018/0289250 A1    Oct. 11, 2018

(30) Foreign Application Priority Data
Oct. 29, 2015    (GB) .................................. 1519117.4

(51) Int. Cl.
*A61B 3/032* (2006.01)
*A61B 3/00* (2006.01)
*A61B 3/06* (2006.01)

(52) U.S. Cl.
CPC ............ *A61B 3/0008* (2013.01); *A61B 3/066* (2013.01); *A61B 3/0091* (2013.01)

(58) Field of Classification Search
CPC ..... A61B 3/032; A61B 3/0025; A61B 3/0041; A61B 3/0033; A61B 3/036
(Continued)

(56) References Cited

U.S. PATENT DOCUMENTS

2006/0227290 A1   10/2006  Murray et al.
2006/0262272 A1*  11/2006  Anderson .............. A61B 3/066
                                                              351/221

(Continued)

FOREIGN PATENT DOCUMENTS

CN    104 765 162 A    7/2015
GB    2 246 427 A      1/1992

OTHER PUBLICATIONS

International Search Report dated Jan. 17, 2017, in International Application No. PCT/GB2016/053301; Filed: Oct. 21, 2016; Applicant: University of Essex Enterprise Limited.
(Continued)

*Primary Examiner* — Mohammed A Hasan
(74) *Attorney, Agent, or Firm* — Erise IP, P.A.

(57) ABSTRACT

A visual stress assessment device is provided comprising a plurality of coloured light sources, each adapted to produce light of a predetermined hue, and a white light source. The white light source and the coloured light sources each comprise a plurality of light emitting diodes. A chamber is provided having an interior comprising a viewable region configured to provide a sample for inducing visual stress, wherein said viewable region is arranged to be illuminated by the white light source and the coloured light sources. A controller is configured to selectively operate the white light source and coloured light sources such that only one or both of a first of the coloured light sources and a second of the coloured light sources are operated simultaneously with the white light source, whereby their respective emitted light is observable in the viewable region by a user at a predetermined hue and saturation.

20 Claims, 5 Drawing Sheets

(58) Field of Classification Search
USPC .......................................................... 351/239
See application file for complete search history.

(56) References Cited

U.S. PATENT DOCUMENTS

| | | | |
|---|---|---|---|
| 2007/0139611 A1* | 6/2007 | Anderson .............. | A61B 3/066 351/200 |
| 2012/0187838 A1* | 7/2012 | Hanna .................. | G06K 9/2027 315/76 |
| 2015/0092027 A1* | 4/2015 | Nishiwaki ............ | H04N 13/307 348/54 |

OTHER PUBLICATIONS

Written Opinion of the International Searching Authority dated Jan. 17, 2017, in International Application No. PCT/GB2016/053301; Filed: Oct. 21, 2016; Applicant: University of Essex Enterprise Limited.

* cited by examiner

VISUAL STRESS ASSESSMENT DEVICE

RELATED APPLICATIONS

The present application is a national stage application under 35 U.S.C. § 371 of International Application No. PCT/GB2016/053301, filed 21 Oct. 2016, which claims priority to Great Britain Patent Application No. 1519117.4, filed 29 Oct. 2015. The above referenced applications are hereby incorporated by reference into the present application in their entirety.

FIELD OF THE INVENTION

The present invention relates to a visual stress assessment device. An example application of the invention is in the selection of tinted lenses for the treatment of visual stress.

BACKGROUND TO THE INVENTION

Interest has been building to find an effective treatment for migraines and to address their underlying cause in persistent migraine sufferers. Research is growing to link migraines with visual discomfort, often associated with perceptual distortions, particularly in printed text. This is commonly referred to as visual stress, photophobia or Meares-Irlen syndrome. These perceptual distortions typically occur where the text appears to move and blur, resulting in eye-strain, headaches and reading difficulties. The condition is estimated to be present in about 40% of poor readers and in at least 5% of the general population in varying degrees.

It has been shown that the use of eyewear containing 'precision tinted lenses' can prevent, or at least reduce, symptoms of visual stress experienced by a patient, making it easier for the patient to read without discomfort. Some migraine sufferers report that they can prevent or curtail their aura by wearing their precision tints.

The Intuitive Colorimeter®, manufactured and distributed by Cerium Visual Technologies Limited (Company No. 02817206) is an example of a visual stress assessment device used for the precision selection of tinted lenses and is now in widespread optometric use in the UK and overseas. The Mark 1 version of the device is described in GB-B-2246427, whilst the Mark 2 and 3 versions are described in EP-B1-0803679. The basic principle of its use is as follows; the device illuminates a page of text with coloured light of a given spectral power distribution (loosely referred to as 'tint') which is observed by a patient. The spectral power distribution refers to the distribution of light energy or power across the visible spectrum. An optometrist varies the tint of the coloured light by adjusting its hue and saturation independently until a tint has been selected that most reduces any visual discomfort experienced by the patient. Bespoke software is then used to select an appropriately dyed lens to match the selected tint which reduces perceptual distortions and increases reading fluency.

A detailed discussion of the Intuitive Colorimeter® (Mark 2) and its merits is provided in Wilkins, A. J. and Sihra, N. (2001), *A colorizer for use in determining an optimal ophthalmic tint. Color Res. Appl.*, 26: 246-253. In summary, a mechanical system is used for colour mixture in which seven coloured filters are equally disposed around the circumference of a cylinder. Light from a fluorescent lamp within the cylinder passes through two neighbouring filters via a square aperture into a viewing chamber where it is mixed by multiple reflection. The proportion of light transmitted through the filters varies with the rotation of the cylinder, continuously changing the hue. The cylinder can slide along its axis bringing a third (neutral grey) filter into the aperture, reducing the saturation of the colour. Attenuation filters can also be inserted or removed so as to adjust the luminance (i.e. brightness) of the light reflected from within the chamber.

Part of the ingenuity of the Intuitive Colorimeter® is its ability to enable independent variation in hue, saturation and luminance such that any tint can be produced within a wide gamut. The variation in the colour or 'tint' produced by the device is continuous, rather than necessarily occurring in discrete steps, enabling the best possible tint to be selected. The spectral power distribution of the light produced in the instrument also substantially matches that obtained from tinted spectacle lenses worn under conventional fluorescent lighting. This feature is nontrivial considering that coloured light is combined in an additive manner within the device, whereas it is combined in a subtractive manner in dyed spectacle lenses.

AU-A1-2006236057 discusses a number of limitations which are identified in the Intuitive Colorimeter®; namely its size, its mechanical nature and the need for a skilled operator to be present to control it. An alternative method and apparatus is suggested that attempts to address these limitations by providing an electronic display device wherein the step of selecting a tint (including modifying the saturation, luminance and hue independently) is computer implemented. The display device utilised is a liquid crystal display (LCD), connected to a standard computing system. The methods by which the hue and saturation are manipulated are not described, and are critical, partly because the chromaticity of the screen needs calibration if the hue and saturation are indeed to be manipulated separately at a constant luminance. It is not possible to achieve a spectral power distribution from an LCD (which inherently comprises red, green and blue pixels only) such that it matches the spectral power distribution obtained when coloured filters are worn under conventional light sources, at least those filters that use conventional dyes.

There is therefore a need for an improved device that addresses the abovementioned limitations in the prior art.

SUMMARY OF THE INVENTION

In accordance with a first aspect of the invention there is provided a visual stress assessment device comprising:
- a white light source and a plurality of coloured light sources, each coloured light source adapted to produce light of a predetermined hue, wherein each of the white light source and coloured light sources comprises a plurality of light emitting diodes;
- a chamber having an interior comprising a viewable region configured to provide a sample for inducing visual stress, wherein said viewable region is arranged to be illuminated by light from each of the white light source and plurality of coloured light sources when in use; and
- a controller configured to selectively operate the white light source and coloured light sources such that only one or both of a first of the coloured light sources and a second of the coloured light sources are operated simultaneously with the white light source, whereby their respective emitted light is observable in the viewable region by a user at a predetermined hue and saturation.

The present invention provides an improved device for producing light of a desired spectral power distribution or 'tint' by overcoming the limitations in the prior art discussed above. Primarily, unlike the Intuitive Colorimeter® Mark 1-3, the device has no moving parts, yet is also able to individually vary the hue, saturation and luminance independently so as to produce any tint within a wide gamut to the required precision. The lack of moving parts improves the reliability of the device, decreases its size and decreases the manufacturing costs. Furthermore the device is also controlled using a controller that can be automated, rather than necessarily requiring an optometrist to manually operate it. This increases the ease and the potential accuracy with which the device can be used.

The controller is preferably an electronic controller for operating the device in response to one or more manual user controls, or instructions embodied in circuitry or software. Typically the controller comprises one or more processors in communication with the light sources. The one or more processors may reside on a PC or other computer device. Furthermore, the controller may be integral with the device itself, or reside on an external computing system to which the remainder of the device is connected. It is preferred that the operation of the device is generally automated in terms of at least controlling one or more of the hue, saturation and luminance and in particular a sequence embodying variation of these parameters.

The device is provided primarily to aid a user, usually in association with a suitably trained professional, in determining whether or not the symptoms of visual stress, which the user may typically experience particularly when reading, are reduced under certain tints of light. A viewable region is therefore provided within the device, which is configured to be illuminated by the light sources and provide a sample for inducing visual stresss. This sample may comprise readable or non-readable material, however typically it contains text consisting of randomly ordered common words arranged in a paragraph, provided on paper or card.

It is desirable to ensure that the spectral distribution of the light produced by the device substantially matches what would achieved by a patient wearing tinted lenses either in daylight or under conventional man-made light sources. Light emitting diodes (LEDs) are a good approximation to daylight in so far as they produce a relatively broad spectrum of light with fewer isolated large spectral lines than fluorescent sources. LEDs are also becoming increasingly popular for use as normal indoor lighting and will shortly be representative of conventional manmade light sources also. Furthermore, unlike incandescent bulbs, the luminance of LEDs can be adjusted without significantly affecting the spectral distribution of the light they emit. This property is particularly advantageous as it provides a means by which the device can independently vary the hue, saturation and luminance of the light produced, as will later become evident.

The controller is preferably further configured to modulate (i.e. vary) said predetermined hue and saturation using only one or more of the first of the coloured light sources, the second of the coloured light sources, and the white light source. This enables the device to precisely vary the tint of the light in which the sample is illuminated so that a user may assess whether their symptoms of visual stress have improved or worsened.

As the tint (spectral power distribution) varies, the device user may provide an input to the device relating to their perceived level of visual stress. A benefit is provided wherein the controller is further configured to receive inputs from an input device corresponding to the visual stress experienced by a user viewing the sample illuminated at a plurality of different tints, wherein each tint has a predetermined hue and saturation.

The device may be used to suggest a particular lens having a corresponding ophthalmic tint, that reduces the effects of visual stress for that user. A further benefit is therefore provided wherein said controller is configured to output onto a display lens data for reducing visual stress based on the visual stress inputs provided by a user. This display may comprise, for example, a computer monitor.

In order to best simulate what would be perceived by a patient wearing uniformly tinted lenses, the white and coloured light sources are preferably each arranged within the chamber such that light emitted from the white and coloured light sources is evenly dispersed onto the viewable region. Thus, it is desirable to produce diffuse or homogeneous illumination. The white light source and the plurality of coloured light sources may be arranged in a number of different ways to achieve this, however preferably they are grouped together, for example on a panel since this assists in the manufacture and maintenance. Nevertheless, individual LEDs or groups of LEDs comprising part of a particular light source may be physically distributed at different positions within the panel, or indeed within one or more inner walls of the chamber. For example, two identical sets of coloured and white light sources may be provided on separate walls inside the chamber. In order to evenly disperse the light onto the viewable region, the interior of the chamber preferably comprises matte white walls for reflecting and scattering the coloured light within the chamber. Fresnel lenses, prisms or a variety of other apparatus commonly used in optics may also be used to increase the dispersion of the light such that the light reflected from the viewable region is of a substantially uniform tint or spectral power distribution.

The plurality of coloured light sources preferably comprises six or more coloured light sources, each coloured light source being adapted to produce light of a different predetermined hue respectively. This enables a large gamut of coloured light to be produced, and is not possible, for example, using LCDs which have only red, green and blue pixels. By providing six or more coloured light sources that can be selectively operated in the manner described above, the hue of the coloured light can also be varied in a near continuous manner, such that the spectral power of the illuminating light can be manipulated so as to emulate the spectral power experienced when wearing tinted lenses. A number of different coloured sources higher than the three or four conventionally used effectively increases the number of degrees of freedom with which the spectral power distribution may be varied, fascilitating the emulation of the spectral power when wearing tinted lenses. Preferably still where a first and a second coloured light source are illuminated together, the second coloured light source which is illuminated is one of either of two coloured light sources adapted to produce a hue that is spectrally closest to (i.e. either side of) the hue produced by the first coloured light source, out of the selection of coloured light sources provided, according to a hue circle in a chromaticity diagram.

The coloured light sources are adapted to produce light of a predetermined hue (at a maximum saturation) and may be selectively operated by the controller to vary said hue. The predetermined hue produced by each coloured light source has a predetermined spectral power distribution. The white light source may be selectively operated by the controller in addition to the first or first and second coloured light sources so as to adjust the saturation of the coloured light within the chamber and hence adjust its spectral power distribution.

As discussed, it is desirable to ensure that the spectral distribution of the coloured light produced by the device substantially matches what would be achieved by wearing tinted lenses. Preferably, therefore, each coloured light source comprises light emitting diodes which emit a white light and a coloured filter adapted so as to filter the emitted white light and thereby produce the said light of predetermined hue from the white light. Similarly, the white light source preferably comprises light emitting diodes which emit a white light and a neutral filter adapted so as to filter the emitted white light. The neutral filter may filter the emitted white light so as to have a luminance similar to that of the coloured light sources. The LEDs provided within each of the coloured light source and the white light source preferably each have the same (or at least a similar) luminance output in response to the same power input. More preferably, these LEDs are of the same type. Preferably still the LEDs are similar to those used for domestic and office lighting.

The white light emitting LEDs preferably act as a broadband source emitting light across the visible spectrum from about 400 to 700 nm so as to produce white light. This can be achieved, for example, using phosphor-based LEDs. Neutral filters may help ensure that the luminance of the light emitted from each active LED within the white light source is substantially equal to the luminance of light emitted from each active LED within the first and second coloured light sources. This property is desirable for achieving a constant overall luminance during saturation or hue modulation.

LEDs which emit a coloured light without the need for a filter could potentially be used within the coloured light sources instead however these coloured LEDs have not yet been produced for a sufficiently large variety of hues to enable any tint within a wide gamut to be produced, as required. Furthermore, the spectral distribution of the coloured light emitted by coloured LEDs is typically not appropriate to mimic the spectral distribution transmitted by tinted lenses when these are worn under conventional indoor lights.

Neutral and coloured filters in combination with white light LEDs are therefore preferred to produce the white and coloured light sources. The dye used to produce the coloured and neutral filters is preferably chosen such that, when used in combination with white LEDs, the spectral distribution of the output light is smooth, contains minimal unwanted isolated peaks or troughs and mimics that obtained when a similar white light source is observed through lenses tinted using these dyes.

The controller is preferably adapted such that the overall luminance of the light emitted by the white light source and the first and second coloured light sources collectively is held constant. This is typically desired when controlling the hue and/or saturation, however the device may be further adapted for enabling overall luminance control. This may be achieved, for example using additional neutral filters or by collectively varying the duty cycle with which the LEDs are lit using the controller.

A luminance of 30 $cd \cdot m^{-2}$ is typically required for the tinted light reflected from the visible region to be appropriate for reading, matching the light levels typically available in an office setting when wearing tinted lenses. Moreover, any filters used may remove approximately 80% of the light emitted by the LEDs. Therefore, in order to ensure that a sufficient amount of light is reflected from the viewable region of the device to be detected by the human eye it is desirable to use at least ten light emitting diodes within each coloured light source and at least ten light emitting diodes within the white light source. This enables a range of luminance levels to be achieved, for each light source, from high luminance to low luminance, whilst ensuring that the light is evenly dispersed within the chamber. As should be evident, the exact number of LEDs required is dependent on the maximum luminance achievable by each LED and on the absorption properties of the device. Each LED is preferably illuminated at a constant voltage, with the luminance increased or decreased by changing the number of LEDs that are illuminated, however alternatively the power supplied to the LEDs or each LED may be incrementally varied so as to vary the overall luminance (in practice this typically requires the power to be varied rapidly over time). In the event that there are two identical sets of coloured and white light sources, at least twenty light emitting diodes may be provided overall for each coloured region of a predetermined hue and at least twenty light emitting diodes may be provided for the white or neutral region. In another advantageous arrangement sixteen light emitting diodes are provided overall for each coloured region of a predetermined hue and at sixteen light emitting diodes are provided for the white or neutral region.

The viewable region preferably comprises a stage configured to support a sample. Preferably the sample is a text sample wherein text has been written or printed onto a surface. The stage may comprise, for example, a ledge, clips, a slit, or a magnetic surface onto which paper, card or a plate (for example) displaying the text can rest. Alternatively, text may simply be printed, written or otherwise imprinted onto the stage itself within the viewable region. Preferably still, said viewable region is viewable from a position outside of the chamber. For example, the patient may be seated in a darkened room besides the device viewing the viewable region within the chamber through a window or aperture in the device.

A particular benefit is realised when the device further comprises one or each of a rotary wheel switch and a slider switch for operating the controller. This allows a patient using the device and viewing the viewable region to manually vary the light produced, if required, without the need for separate visual reference to a control that could alternatively be provided on a touchscreen display or computer for example.

In accordance with a second aspect of the invention there is provided a method for assessing visual stress using a device according to the first aspect of the invention, the method comprising:

(i) producing light of a predetermined hue and saturation using the first coloured light source, or the first and the second coloured light sources so as to illuminate the viewable region;

(ii) producing white light from a white light source and modulating said white light at said predetermined hue so as to illuminate the viewable region together with the light of said predetermined hue and modulate the saturation of said coloured light;

(iii) recording a user response to the illumination of the viewable region in accordance with steps (i) and (ii) from a user observing the viewable region; and (iv) repeating steps (i) to (iii) for a plurality of predetermined hues.

The method according to the invention enables the independent control of the hue, saturation and luminance so as to illuminate the viewable region with coloured light of various different tints. The hue of the light is selected by producing light from a first coloured light source, or a first and a second coloured light source. This light then reflects off the inner walls of the chamber and combines in an additive manner. The saturation can then be varied at this hue by increasing or decreasing the light emitted from the white light source.

In order to ensure the luminance of the light is constant, for example whilst varying the hue or saturation, the power supplied to the light emitting diodes is preferably held constant. This could most simply be implemented by ensuring that the same number of LEDs are lit at any one time. Alternatively, the power supplied to the LEDs may be modulated accordingly and the different attenuating properties of each filter could be accounted for. This power control is typically implemented by the controller. Step (ii) therefore preferably further comprises modulating the luminance of the light emitted by the first, or first and second, coloured light sources in accordance with the luminance of the light emitted by the white light source such that the overall luminance emitted by the coloured and white light sources into the chamber remains constant.

A user of the device preferably views a sample which is displayed in the viewable region and illuminated at a predetermined hue. The saturation is then typically adjusted at this hue and the user's subjective response to the visual comfort of the hue and the saturation level is recorded. The user responses are typically recorded on a computer, which may form part of, or be connected to the controller, using a standard input device such as a keyboard, mouse or touchscreen and dedicated software for processing and recording the inputs. The hue is then typically varied by a predetermined amount around the hue circle at which point, the saturation is varied and the user's response is once again recorded. It is preferable to perform this hue control when the light is least saturated (i.e. most white) as this has generally been found to be more comfortable to the user. The process may be repeated across the full 360 degrees of hue until the original hue is once again reached. In theory, the saturation may initially be held constant whilst the hue is varied instead however experience has shown the former method to be more effective.

The method preferably further comprises (v) analysing the user responses obtained at step (iii) and selecting a candidate spectral power distribution in accordance with said analysis. The candidate spectral power distribution is also referred to herein as the candidate tint and preferably comprises a hue and a saturation which together most alleviate the symptoms of visual stress and increase reading fluency. Multiple candidate tints may be selected or proposed for comparison against one another by the user. In the event there is ambiguity in the results and it is difficult to determine an optimum hue, a hue may be selected that is approximately complementary (i.e. the opposite hue in the hue circle) from whichever hue was least comfortable to the user. If the appropriate saturation level cannot be determined an arbitrary saturation may be chosen.

The method preferably further comprises: (vi) producing light of the candidate spectral power distribution using the first coloured light source, or the first and the second coloured light sources, and using the white light source; (vii) modulating either or each of the hue and the saturation from said candidate spectral power distribution; and (viii) selecting a desired spectral power distribution based on feedback received from the user observing the viewable region in accordance with step (vii).

The candidate spectral power distribution represents a first estimate of the optimum hue and saturation that best reduces visual stress in the device user. After this tint has been selected and is subsequently reproduced by the device, the user is encouraged to 'fine tune' the selection by manually varying the hue and saturation so as to improve upon the first estimate and select a desired spectral power distribution or 'tint'.

A particular benefit is realised when the method further comprises outputting data in accordance with said desired spectral power distribution for use in selecting a coloured eyewear lens. This data may comprise, for example, look-up tables for selecting precision tinted lenses, wherein the tint of the lens may be matched to the desired spectral power distribution based on the user responses, or could comprise data that had already been processed using said look-up tables with suggestions on appropriate lenses, alternative lenses or further tests to be performed, having already been made. The data are typically analysed by an optometrist who may check the brightness is appropriate to mimic conventional light sources and perform further tests or adjustments, such as varying the brightness and/or saturation as necessary.

So that the speed, ease and accuracy with which the method can be performed may be increased, the above method steps are preferably computer-implemented and performed using an automated controller. The absence of moving parts, and the ease with which the power supplied to LEDs can be controlled using an automated controller, such as a PC, make the method particularly suitable for computer implementation.

A user may simply follow instructions that are provided on a computer display, for example and input their responses to the various steps using standard computing equipment. This reduces the need for an optometrist to be present to operate the device. The initial process of cycling through various hue and saturation combinations so as to suggest one or more candidate tints may be automatically performed by an automated controller, with occasional feedback being required from the user. The 'fine tuning' stage which follows may also be performed using an automated controller, however, is more preferably performed by the device user viewing the viewable region meanwhile operating the saturation and hue controls him/herself. The controller may monitor the hue, saturation and luminance however so that once a desired tint has been selected, the corresponding hue, saturation and luminance values may be displayed. This can be used by an optometrist when selecting a suitable combination of precision tinted trial lenses, a combination that later specifies the dyeing necessary for the patient's spectacle lenses.

In accordance with a third aspect of the invention there is provided a computer readable medium containing instructions which when executed cause the device of the first aspect to perform the method of the second aspect. Examples of suitable computer readable medium are CD-ROM, hard drives or flash drives containing software for operating the device. The third aspect shares similar advantages as those already discussed with reference to the first and second aspects.

BRIEF DESCRIPTION OF THE DRAWINGS

Examples of the invention will now be described with reference to the accompanying drawings, in which.

DETAILED DESCRIPTION

Figure 1:
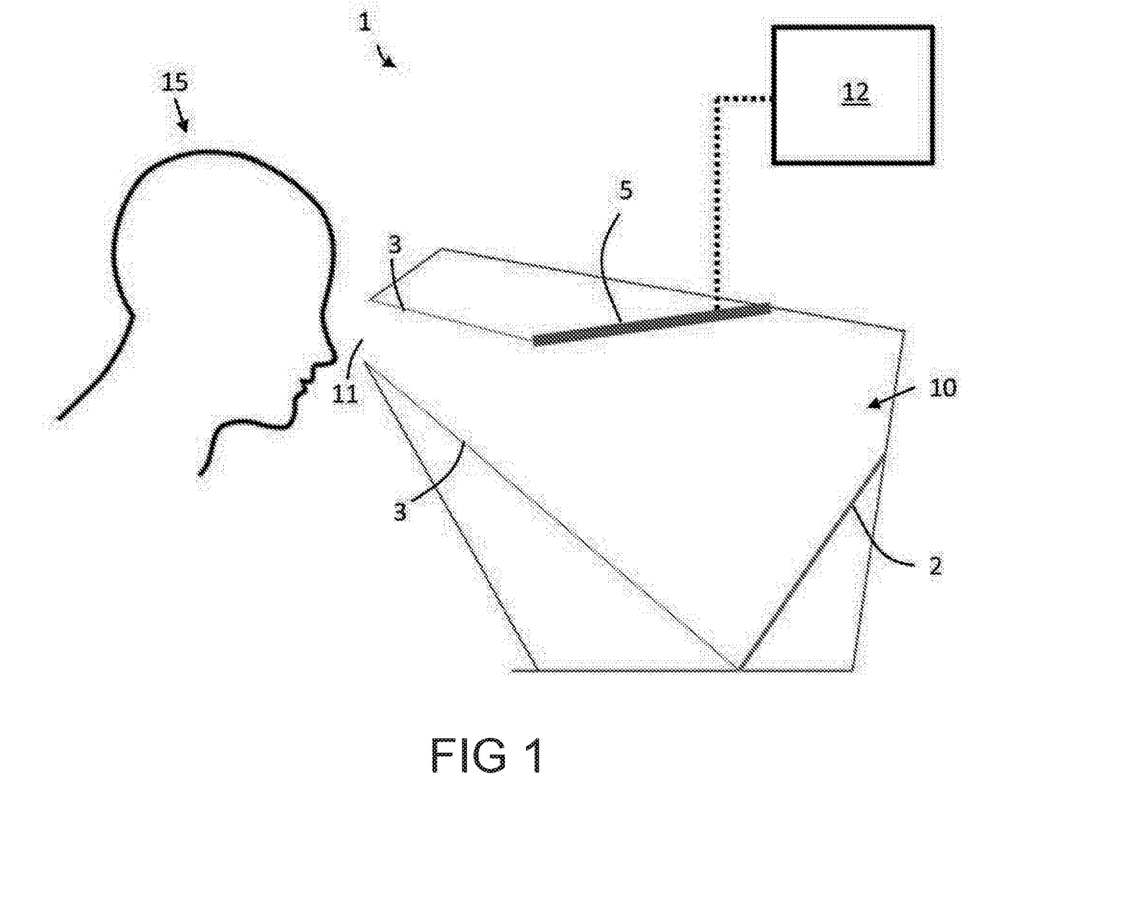
FIG. 1 is an illustration of a device in accordance with an example of the invention.

A visual stress assessment device 1 in accordance with an example of the invention is shown in FIG. 1. The device 1 comprises a chamber 10 having an interior defined by matte white inner walls 3 configured to evenly disperse light by multiple reflection within the chamber 10. A panel 5 of LEDs 6 is provided within the chamber for emitting coloured and white light onto the inner walls 3 and onto the viewable region 2. The viewable region (or stage) 2 is configured to support a sample of text, such as paper, card or a plate onto which text is printed. Although this could be achieved in a variety of ways, in this example a reading plate containing a passage from the Wilkins Rate of Reading Test™ is inserted into the side of the device through an aperture (not shown) so that it is visible within the viewable region 2. A sample is chosen which causes visual stress for the device user using white light (e.g. daylight) when no coloured lenses are worn. The viewable region 2 is viewed by a user 15 from a position outside the device 1 through an aperture or window 11. The chamber 10 and aperture 11 are configured to exclude light from outside of the device 1 so that the viewable region 2 is only illuminated with light provided by the LED panel 5.

The LED panel 5 is operated by a controller 12 which resides on a computing system, for example a computer comprising one or more processors, memory comprising instructions for operating the device and a user input device, such as a mouse, keyboard, display, switches, touchscreen etc. Manual controls (not shown), for example rotary or sliding switches, for adjusting the saturation, hue and luminance are also provided.

Figure 2:
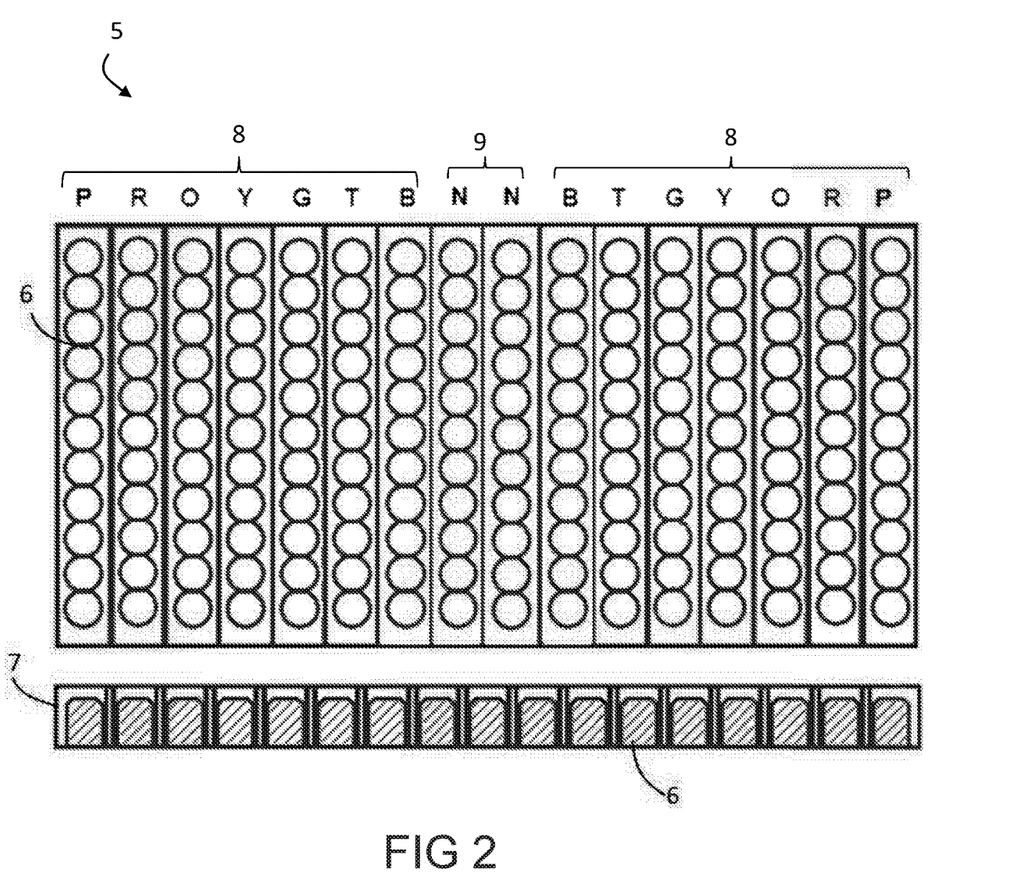
FIG. 2 is an illustration of a coloured light source and a white light source in accordance with an example of the invention.

Alternative views of the LED panel 5 are shown in FIG. 2. A front-on view is shown above and a cross-sectional view is shown below. The panel 5 comprises a plurality of coloured light sources 8 and a white light source 9 as shown. Each coloured light source comprises a plurality of white light emitting LEDs 6, such as phosphor-based LEDs, which are encased in a dyed filter 7 so as to produce light of a predetermined hue within the chamber 10. In this example seven coloured light sources are provided and the hues shown are purple (P), rose (R), orange (O), yellow (Y), green (G), turquoise (T) and blue (B). The white light source 9 also comprises a plurality of white light emitting LEDs 6 encased in a neutral (N), or achromatic grey filter 7 to assist in luminance control such that the luminance of the light emitted by each active LED within the coloured and white light sources into the chamber is approximately equal. In other words, if half of the LEDs were illuminated within the white and yellow regions respectively (each active LED being at a constant brightness) the luminance of the light emitted by the white region would be substantially equal to that emitted by the yellow region. The sum of these luminances (i.e. the overall luminance) typically remains constant when attempting to find a candidate spectral power distribution.

The coloured and white sources each contain 11 LEDs that are linearly arranged and parallel to one another in respective light sources. The panel 5 is arranged in a symmetrical manner married about a centre line. The white light source 9 is provided in the middle and the plurality of coloured light sources 8 are arranged symmetrically either side of this in their spectral order such that each colour is repeated either side of the white light source 9 as shown. Each coloured light source and the white light source hence contain a total of 22 LEDs overall. This configuration produces excellent light dispersion within the chamber 10 that ensures the light incident on, and reflected by, the viewable region 2 is of a homogeneous or uniform tint. Alternative configurations, for example using different LEDs positions, a different number of LEDs, or the use of Fresnel lenses/prisms may be used. For example, each coloured light source and the white light source may contain a total of 16 LEDs overall.

The coloured light sources 8 are arranged according to their chromaticity i.e. in order of their hue angle. It is convenient to refer to the arrangement according to the HSL/HSV cylindrical coordinates in terms of the three independent subjective parameters of colour: hue, saturation and luminance. The hue angle varies from 0 to 360 degrees (with rose at 0 and 360 degrees), whereas the saturation varies from 0 to 100 percent (with neutral grey being 0 percent). Each neighbouring coloured region is adapted to produce light of a different hue at approximately regular intervals along the hue circle, in this case at approximately 50 degree intervals. Intermediate hues that occur between these values (for example, at 25, 75 and 125 degrees) can be produced by illuminating two neighbouring coloured regions, each at the same luminance. Alternatively, the plurality of coloured light sources may contain only 6 coloured regions (i.e. coloured light sources), each region adapted to produce light of a predetermined hue at approximately 60 degree intervals. In order to produce a sufficiently large range of hues it is desirable to have six or more different coloured regions.

An approximate continuum of hues can be achieved by varying the luminance of the light emitted by each of the first and second coloured light sources, for example so that one is brighter than the other. As will be quickly realised, a larger number of LEDs within each coloured and white light source will generally mean a greater variety of hue, saturation and luminance is achievable.

Figure 3:
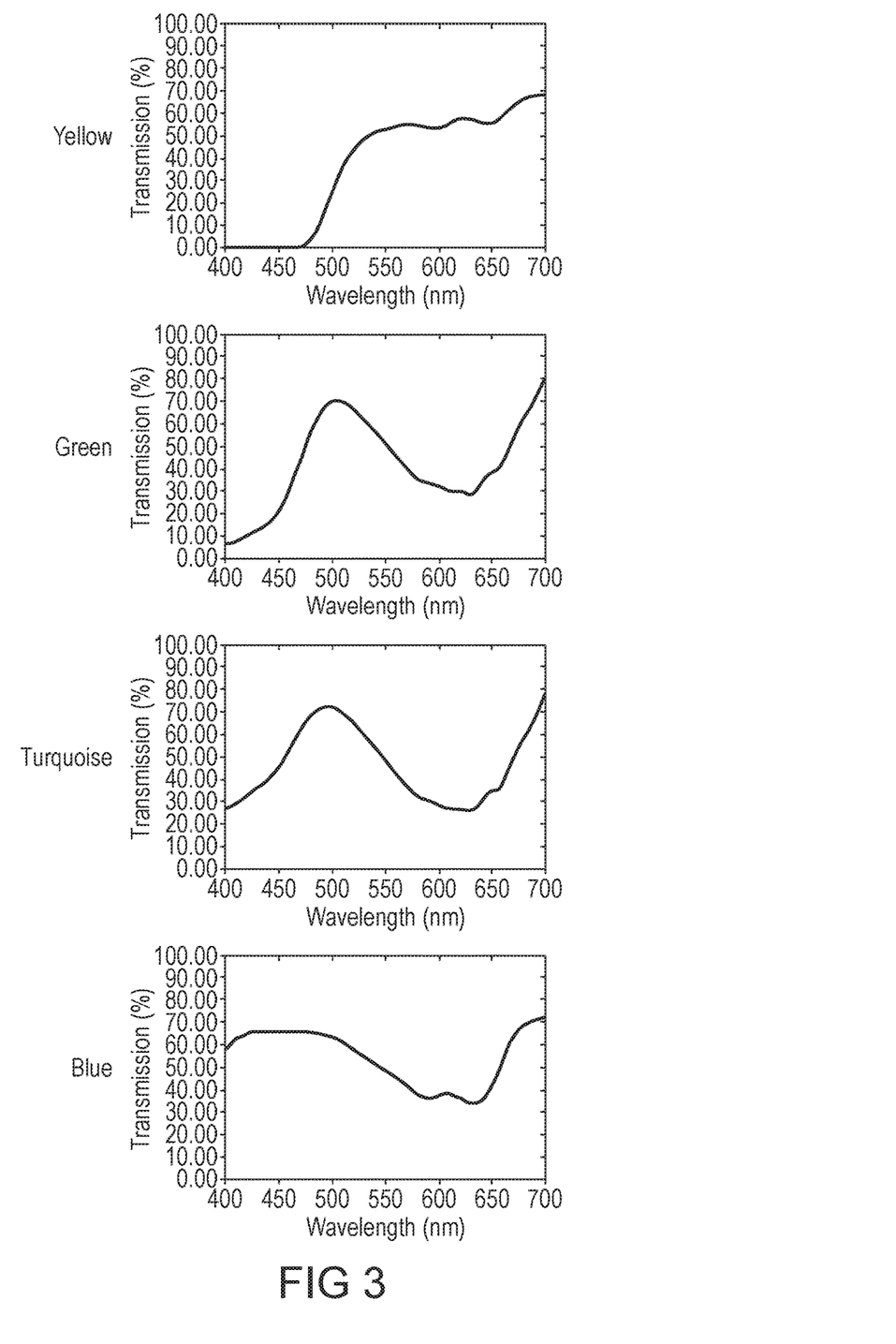
FIG. 3 shows a series of curves representative of the transmission characteristics of different dyed coloured filters; and, FIG. 4 is a flow diagram illustrating a method in accordance with an example of the invention.

The approximate transmission characteristics of each of the filters 7 used on the coloured light sources 8 in the panel 5 are shown in the graphs of FIG. 3. In each graph, the abscissa x-axis shows the wavelength 'λ' of from 400 to 700 nanometres and the ordinate y-axis shows the relative transmission or intensity 'I' of light transmitted through the filter from 0 to 100%. The transmission characteristics of the filters 7 can be varied during their manufacture so that a relatively smooth curve is produced with no unwanted spectral lines that enhance metamerism. The transmission characteristics of the filters 7 can also be chosen so as to compensate for the spectral output of the LEDs 6 that the filters 7 will be used in conjunction with. The relative transmission for the neutral filter used in the white light source 9 is the same for all wavelengths of visible light and so would be represented by a horizontal line in a similar transmission graph.

Selecting a tint that optimally reduces the effects of visual stress is typically a time consuming process when using known device, requiring careful manual control of the hue and saturation. The accuracy with which this process can be performed can be increased and the overall time decreased by using the device and method according to the invention.

Figure 4:
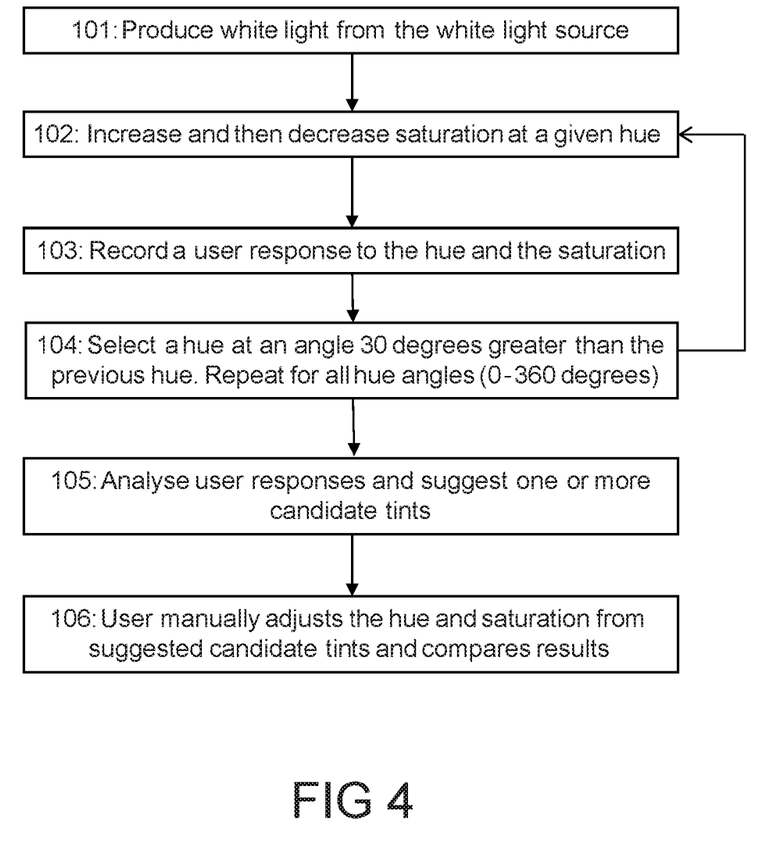

An example of a method according to the invention will now be discussed with reference to the flow diagram of FIG. 4 and the device of FIGS. 1 and 2.

An automated controller 12 is provided, such as a computer comprising a user input device, one or more processors and memory comprising instructions which when executed by the one or more processors causes the device 10, most notably the LEDs 6, to perform the method steps described below. Said instructions may be provided on local memory, such as volatile or non-volatile memory, or stored on removable memory, e.g. a CD-ROM.

At step 101 the controller 12 illuminates all of the LEDs in the white light source only so as to produce white light. The light emitted from the LED panel 5 is scattered off the inner walls 3 of the chamber 10 such that it is evenly dispersed onto the viewable region 2. This viewable region 2 supports a sample (not shown) which is viewed by a user 15 through an aperture 11.

At step 102 the controller 12 increases the saturation of coloured light within the chamber 10 by decreasing the number of LEDs that are lit within the white light source 9 and by increasing the number of LEDs that are lit within one coloured light source or two neighbouring coloured light sources. For example, a hue of 0 degrees may initially be chosen such that only the rose coloured light source is illuminated in combination with the white light source. In this example the LEDs are either illuminated at a constant luminance or not at all, and a constant overall luminance is achieved by ensuring that the same number of LEDs remain lit at any one time. This is a slight approximation given that not all of the filters 7 (and potentially LEDs) used will necessarily be equally efficient however this can be compensated for accordingly.

In an alternative example, the luminance of the light emitted from the LEDs within the coloured light source(s) may be gradually increased, whilst decreasing the luminance of light emitted from the LEDs within the white light source meanwhile ensuring that the total power supplied to the white and coloured light sources in combination remains approximately constant so as to achieve a constant overall luminance.

The saturation is varied over five seconds from a minimum value at 0% saturation (where no power is supplied to the coloured light sources), to a maximum value 100% (where light is emitted by the coloured light source(s) only and not from the white light source). The device remains at this maximum saturation for five seconds and then is decreased again to 0% over another five seconds. At step 103 the user 15 inputs a response to both the hue and the saturation onto the computer using a keyboard which is in communication with the controller. The different tints observed by the user may be graphically displayed on a fan chart with one or many data enty points being taken along the hue circle. Numerical inputs may be used, for example the user 5 may rate how comfortable or uncomfortable a hue is on a scale between +5 to −5, for example, (in which negative numbers represent discomfort, 0 means no difference and positive numbers show improvement). The user 15 will also input a response related to the effect that decreasing the saturation had on their visual comfort when viewing the text sample on the stage 2. This may be done, for example, by the user 15 selecting whether the comfort improved as the saturation was decreased and at approximately what level it was most comfortable.

At step 104, whilst a white light is emitted only, another hue is selected by the controller that is 30 degrees along the hue circle from the previous hue and steps 102 and 103 are repeated for this new hue. In this case both the rose and the neighbouring orange coloured light source regions are lit (however by unequal amounts). The light emitted by the coloured light sources disperses within the chamber 10 so that a uniform hue that is roughly between the hue produced by either source independently is viewed by the user 15. This process is then repeated for a plurality of different hues each at approximately regular intervals of 30 degrees along the hue circle until all of the coloured light sources have been illuminated in turn through 12 presentations.

The results which were inputted by the user are then analysed by the controller 12. The controller 12 then outputs one or more candidate tints i.e. candidate spectral power distributions at step 105 comprising an approximate hue and an approximate saturation which may be selected by the user 15. The analysis could be performed in a number of ways, however preferably the five "most comfortable" hue and saturation combinations are selected. Optionally, hues that are 180 degrees from the least comfortable hues may be preferred by the sorting algorithm used by the controller 12 to select the candidate tints wherever there is ambiguity in the results. This process provides a quick, automated rough estimate of the optimum spectral power distribution that can simply be performed by a user 15, without the need for an optometrist to be present to operate the device (unlike the prior art).

At step 106 the user 15 may select a candidate tint from a display causing the controller 12 to issue a signal to the LEDs 6 such that the selected candidate tint or spectral power distribution is produced within the chamber 10. The user 15 may then manually adjust the saturation and the hue independently from that candidate tint, whilst viewing the viewable region 2, by operating manual switches (not shown), for example a rotary switch for controlling the hue and a slider for adjusting the saturation, provided on the outside of the device 1. This process enables the user 15 to fine tune the tint until the most comfortable tint is selected. Typically the candidate tint is output and then the user 15 will make small adjustments to the hue only. If hue is revised, the saturation may then be optimised once again. The saturation and hue values for this tint are monitored and automatically recorded by the controller 12. This process is repeated for each candidate tint and the selected tints finally compared against one another by the user 15 in order to select a desired spectral power distribution that most reduces the symptoms of visual stress.

Appropriate tinted lenses are then selected by the controller 12 based on the responses provided by the user 15 using software containing look-up tables stored in memory and output on a display. Possible additional tests or alterations may also be output so that the lens is suitable for use in conventional lighting. This may require the brightness and the saturation to be adjusted further until an appropriate tint is found. If a strongly saturated colour has been chosen, this can, for certain colours, only be supplied in a dark lens. It is then necessary to establish a compromise between the saturation required and the darkness that is not desirable. The controller 12 can enable this luminance control by simply varying the number of LEDs that are lit or the overall power supplied to the LEDs 6 in the first coloured source, or the first and second coloured sources, and the white source selected for to produce that spectral power distribution using, for example, a rotary switch provided on the housing of the device 1.

Some patients may have an adverse reaction to certain tints being displayed (referred to here as "adverse tints"). The controller 12 may therefore be configured to receive an input of these adverse tint values from a user. This could be provided by the user at any stage, for example using a computer keyboard. The controller 12 may then ensure that the adverse tints, and optionally a range of tints surrounding these values, are not emitted during operation of the device, for example during any of steps 102, 104 and 105.

The invention claimed is:

1. A visual stress assessment device comprising:
    a white light source and a plurality of coloured light sources, each coloured light source for producing light of a predetermined hue, wherein each of the white light source and coloured light sources comprises a plurality of light emitting diodes;
    a chamber having an interior comprising a viewable region for providing a sample for inducing visual stress to the user, wherein said viewable region is arranged to be illuminated by light from each of the white light source and the plurality of coloured light sources when in use; and
    a controller programmed to selectively operate the white light source and the coloured light sources such that only one or both of a first of the coloured light sources and a second of the coloured light sources are operated simultaneously with the white light source, said controller further programmed to modulate the white light source to thereby independently adjust a saturation of the light from at least one of the coloured light sources projected onto the viewable region, whereby their respective emitted light is observable in the viewable region by a user at a predetermined hue and saturation.

2. A device according to claim 1, wherein said controller is further configured to modulate said predetermined hue and saturation using only one or more of the first of the coloured light sources, the second of the coloured light sources, and the white light source.

3. A device according to claim 2, wherein said controller is further configured to receive inputs from an input device corresponding to the visual stress experienced by a user viewing the sample illuminated at a plurality of different tints, wherein each tint has a predetermined hue and saturation.

4. A device according to claim 3, wherein said controller is configured to output onto a display lens data for the selection of a coloured lens based on the visual stress inputs provided by a user.

5. A device according to claim 1, wherein said white and coloured light sources are each arranged within the chamber such that light emitted from the white and coloured light sources is evenly dispersed onto the viewable region.

6. A device according to claim 1, wherein said plurality of coloured light sources comprises six or more coloured light sources, each coloured light source being adapted to produce light of a different predetermined hue respectively.

7. A device according to claim 1, wherein each colour light source comprises light emitting diodes which emit a white light and wherein each of the said coloured light sources further comprises a coloured filter adapted so as to filter the emitted white light and thereby produce the said light of predetermined hue.

8. A device according to claim 1, wherein the white light source comprises light emitting diodes which emit a white light and wherein the said white light source further comprises a neutral filter adapted to filter the emitted white light.

9. A device according to claim 1, wherein the controller is adapted such that the overall luminance of the light emitted by the white light source and the first and second coloured light sources collectively is held constant.

10. A device according to claim 1, wherein at least ten light emitting diodes are provided within each coloured light source and at least ten light emitting diodes are provided within the white light source.

11. A device according to claim 1, wherein said viewable region comprises a stage configured to support a sample.

12. A device according to claim 1, wherein said viewable region is viewable from a position outside of the chamber.

13. A device according to claim 1, further comprising one or each of a wheel switch and a slider switch for operating the controller.

14. A method for assessing visual stress using a device according to claim 1, the method comprising:
    (i) producing light of a predetermined hue and saturation using the first coloured light source, or the first and the second coloured light sources so as to illuminate the viewable region;
    (ii) producing white light from a white light source and modulating said white light at said predetermined hue so as to illuminate the viewable region together with the light of said predetermined hue and modulate the saturation of said coloured lights;
    (iii) recording a user response to the illumination of the viewable region in accordance with steps (i) and (ii) from a user observing the viewable region; and
    (iv) repeating steps (i) to (iii) for a plurality of predetermined hues.

15. A method according to claim 14, wherein step (ii) further comprises: modulating the luminance of the light emitted by the first, or first and second, coloured light sources in accordance with the luminance of the light emitted by the white light source such that the overall luminance emitted by the coloured and white light sources into the chamber remains constant.

16. A method according to claim 14, further comprising:
    (v) analysing the user responses obtained at step (iii) and selecting a candidate spectral power distribution in accordance with said analysis.

17. A method according to claim 16, further comprising:
    (vi) producing light of the candidate spectral power distribution;
    (vii) modulating either or each of the hue and the saturation from said candidate spectral power distribution; and
    (viii) recording a user response to the illumination of the viewable region in accordance with steps (vi) and (vii) from the user observing the viewable region so as to obtain a desired spectral power distribution.

18. A method according to claim 17, further comprising outputting data in accordance with said desired spectral power distribution for use in selecting a coloured eyewear lens.

19. A method according to claim 14, wherein said method steps are computer-implemented using an automated controller.

20. A computer readable medium containing instructions which when executed cause the device to perform the method of claim 14.

* * * * *